US00PP23922P3

(12) United States Plant Patent
Kardos

(10) Patent No.: US PP23,922 P3
(45) Date of Patent: Sep. 24, 2013

(54) *LAGERSTROEMIA* PLANT NAMED 'CORAL MAGIC'

(50) Latin Name: ***Lagerstroemia* hybrid**
Varietal Denomination: Coral Magic

(75) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 90 days.

(21) Appl. No.: 13/373,363

(22) Filed: Nov. 10, 2011

(65) Prior Publication Data

US 2013/0125276 P1 May 16, 2013

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP16,917 | P2 | 8/2006 | Dirr |
| PP17,411 | P2 | 2/2007 | Dirr |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| 2013/0007933 | P1 | 1/2013 | Kardos |

OTHER PUBLICATIONS

Plant Introductions, Inc. webpage, (downloaded Nov. 3, 2011) "*Lagerstroemia*" selections, http://www.plantintroductions.com/lagerstroemiaselections.html, Plant Introductions, Inc., 6 pages.

*Lagerstroemia* Coral Magic Catalog Page (distributed at a trade show Jan. 5, 2011) Plant Introductions, Inc., 1 page.

*Primary Examiner* — Kent L Bell
(74) *Attorney, Agent, or Firm* — Lathrop & Gage LLP

(57) ABSTRACT

A new and distinct cultivar of *Lagerstroemia* plant named 'Coral Magic', characterized by its compact, rounded to upright intermediate growth habit, reddish new growth, dark green foliage in summer, salmon-pink flowers, and resistance to powdery mildew and *Cercospora* leaf spot.

3 Drawing Sheets

Genus and species of plant claimed: *Lagerstroemia* hybrid. Variety denomination: 'Coral Magic'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'Coral Magic'. 'Coral Magic' is grown primarily as an ornamental for landscape use and for use as a potted plant.

'Coral Magic' originated from open-pollinated seed of 'Gamad VI' (U.S. Plant Pat. No. 22,161) growing in Watkinsville, Ga. The cultivar 'Coral Magic' originated and was selected in a cultivated environment in Watkinsville, Ga. from the progeny of this open-pollination by continued evaluation for growth habit and foliage and flower characteristics.

Asexual reproduction of 'Coral Magic' by stem cuttings in Watkinsville, Ga. since 2009 has shown that all the unique features of this new *Lagerstroemia*, as herein described, are stable and reproduced true-to-type through successive generations of such asexual propagation.

SUMMARY OF THE INVENTION

Plants of the new cultivar 'Coral Magic' have not been observed under all possible environmental conditions. The phenotype may vary somewhat with changes in light, temperature, soil and rainfall without, however, any variance in genotype.

The following traits have been repeatedly observed and are determined to be unique characteristics of 'Coral Magic'. These characteristics in combination distinguish 'Coral Magic' as a new and distinct cultivar: 1. Compact, rounded to upright intermediate growth habit; 2. Reddish new growth; 3. Dark green foliage in summer; 4. Salmon-pink flowers; 5. Resistance to powdery mildew and *Cercospora* leaf spot.

Plants of 'Coral Magic' differ from plants of the parent, 'Gamad VI' (U.S. Plant Pat. No. 22,161), primarily in timing of flowering and flower color. Plants of 'Gamad VI' flower earlier than plants of 'Coral Magic'. Plants of 'Gamad VI' have deep red-purple flowers, whereas plants of 'Coral Magic' have salmon-pink flowers. 'Coral Magic' can also be compared to the cultivar 'GAMAD VIII' (U.S. Plant Pat. No. 23,499), but differs in flower color and flowering time. 'Coral Magic' salmon-pink flowers and flowers later than 'GAMAD VIII', which has pale pink flowers. 'Coral Magic' can also be compared to the cultivar 'Whit VIII' (U.S. Plant Pat. No. 16,616), but differs in flower color and overall size. 'Coral Magic' has salmon-pink flowers and an overall smaller growth habit than 'Whit VIII', which has soft pink flowers.

BRIEF DESCRIPTION OF THE DRAWINGS

The accompanying color photographs illustrate the flower and foliage characteristics and the overall appearance of 'Coral Magic', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
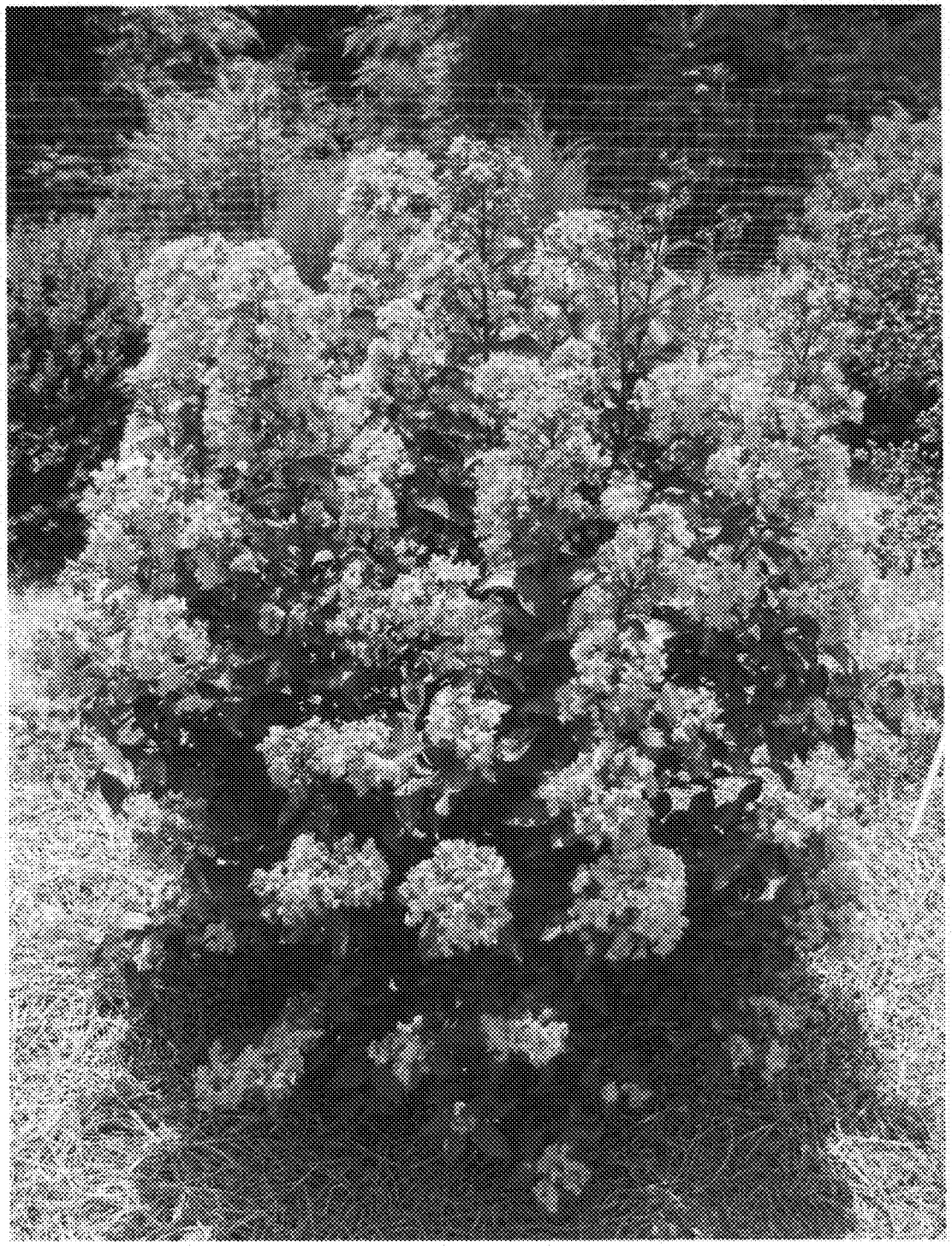
FIG. 1 illustrates the overall appearance of a mature plant of 'Coral Magic' planted in the ground.
Figure 2:
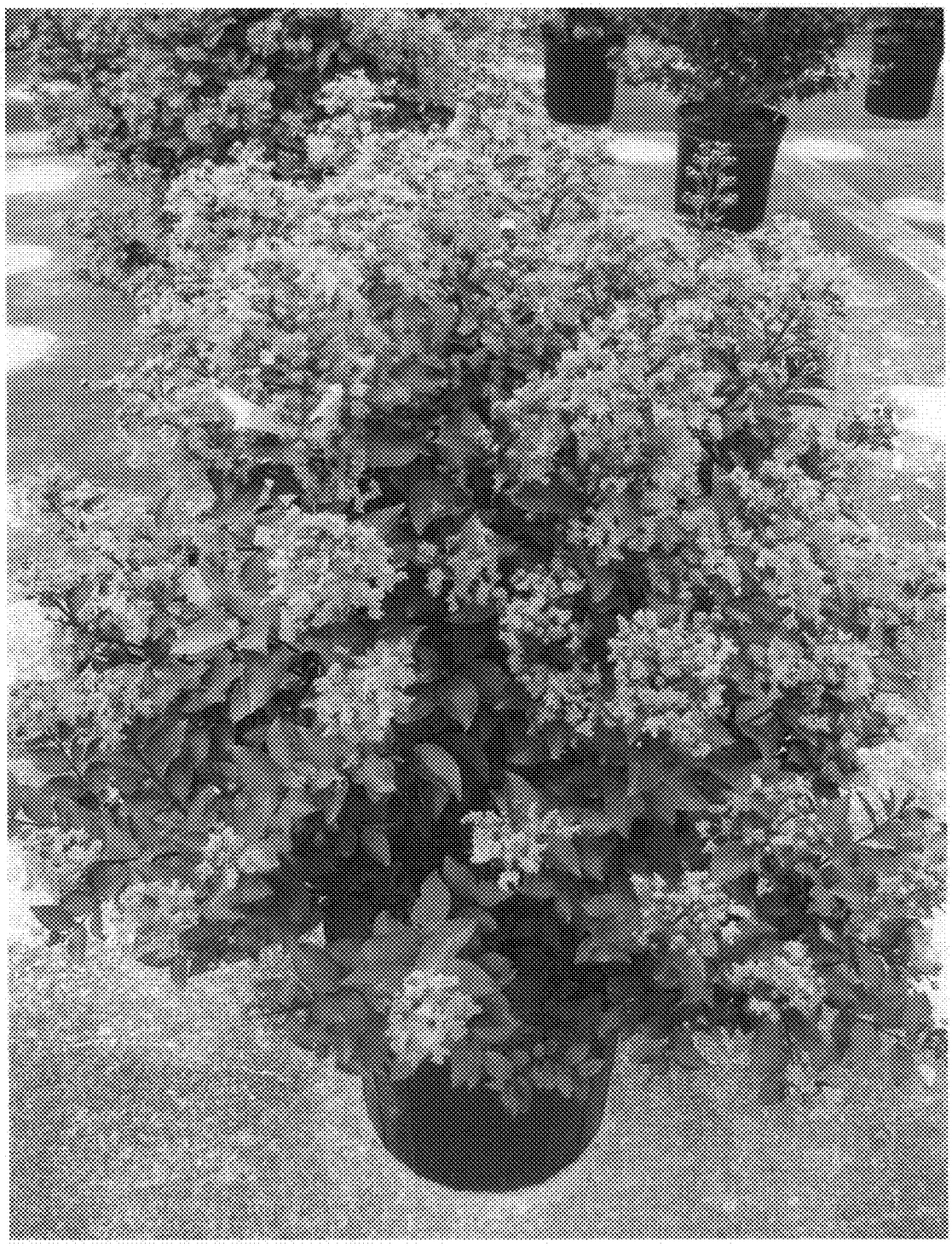
FIG. 2 illustrates the overall appearance of a plant of 'Coral Magic' in a container.
Figure 3:
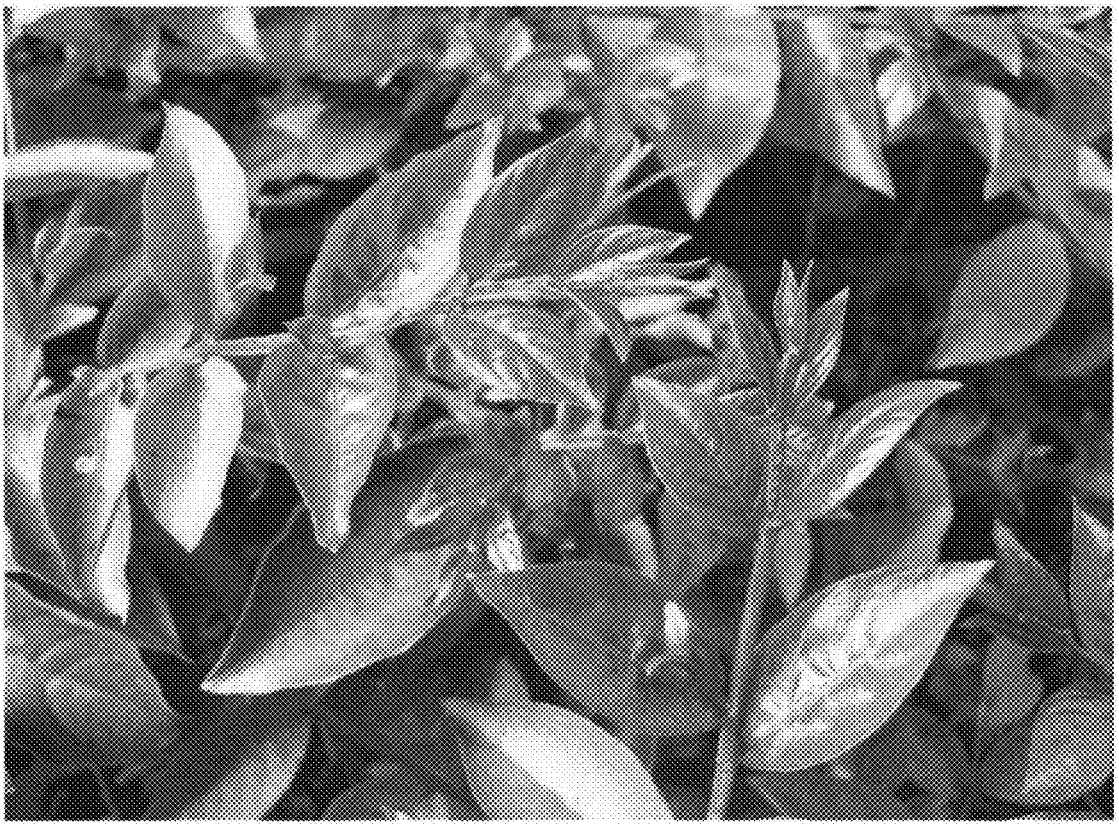
FIG. 3 illustrates a close-up view of the new growth of 'Coral Magic'.

In the following description, color references are made to The Royal Horticultural Society Colour Chart, 2001 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'Coral Magic'.

Parentage:

*Female, or seed, parent.*—*Lagerstroemia* 'Gamad VI' (U.S. Plant Pat. No. 22,161).

*Male, or pollen parent.*—Unknown (open-pollinated).

Propagation: Terminal cuttings.

Time to initiate roots, summer: About 21 days at 32° C.

Plant description:

*Flowering shrub.*—Compact, rounded to upright growth habit. Freely branching; pruning enhances lateral branch development.

*Root description.*—Numerous, fine, fibrous and well-branched.

*Plant size.*—The original plant, now about four-years-old in the ground, is about 91 cm high from the soil level to the top of the inflorescences and about 82 cm wide. First year stems have a diameter of about 2 mm. Shape: squarish. Second year and older stems have a diameter of about 5 mm or more. Shape: round.

*Trunk diameter.*—3 cm at the soil line. Color: 199B.

*Internode length.*—About 1.8 cm.

*Strength.*—Flexible when young, easily broken once mature.

*First year stem color* (*young*).—187A. Color (woody): 199B.

*Second year and older stem color.*—199B.

*Bark.*—Exfoliates in strips beginning on second or third year stems.

Vegetative buds: Sub-opposite to alternate in arrangement, imbricate, conical, with no pubescence.

*Color.*—178A.

*Size.*—About 2 mm in length and 1 mm in width.

Foliage description:

*Arrangement.*—Sub-opposite to alternate, simple.

*Length.*—About 4.3 cm.

*Width.*—About 2.1 cm.

*Shape.*—Elliptical.

*Apex.*—Acuminate.

*Base.*—Cuneate.

*Margin.*—Entire.

*Texture* (*upper and lower surfaces*).—Glabrous and glossy in developing foliage, and glabrous in fully expanded foliage.

*Venation pattern.*—Pinnate.

*Venation color of emerging foliage* (*upper and lower surfaces*).—181B.

*Venation color of fully expanded foliage* (*upper surface*).—178B.

*Venation color of fully expanded foliage* (*lower surface*).—166C.

*Color in developing foliage* (*upper and lower surfaces*).—183A.

*Color in fully expanded foliage* (*upper surface*).—147A.

*Color in fully expanded foliage* (*lower surface*).—146B.

*Petiole length.*—About 2 mm.

*Petiole diameter.*—About 1 mm.

*Petiole color* (*upper and lower surfaces*).—183B.

*Pubescence.*—None.

Flower description: Flowers are produced from about June to September in Watkinsville, Ga. An inflorescence is showy for about two weeks, and individual flowers last about one day and are self-cleaning.

*Inflorescence type.*—Panicle.

*Inflorescence length.*—About 10 cm.

*Inflorescence width.*—About 7 cm.

*Peduncle.*—About 8 cm in length, about 2 mm in diameter, color is 187B, and no pubescence.

*Individual flowers.*—About 2 cm by 3.5 cm.

*Flower buds.*—Length: about 7 mm; Diameter: about 7 mm; Color: 179A.

*Pedicels.*—About 7 mm in length, 183C in color, and no pubescence. Pedicel diameter is about 1 mm.

*Sepals.*—6 per flower, about 8 mm in length, about 5 mm in width, acute apex, entire margin, and 180B in color on upper and lower surfaces.

*Calyx.*—About 8 mm in length, about 8 mm in diameter, 180B in color, and no pubescence.

Petals:

*Arrangement/appearance.*—Usually 6 or 7 per flower.

*Petal length.*—About 1.7 cm.

*Petal width.*—About 1.2 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are 61D.

Stamens:

*Quantity/arrangement.*—About 25 to 30 short stamens clustered in the center, about 8 mm long, filament color is 11D, and anther color is 13B. The short stamens are surrounded by 6 longer stamens, about 1.2 cm long, filament color is 55C, and anther color is 165C. The stamens are not pubescent.

*Pollen.*—Produced in moderate quantities and is 13B in color on the short stamens and 144B in color on the long stamens.

Pistils:

*Quantity.*—One superior pistil per flower.

*Pubescence.*—None.

*Pistil length.*—About 1.7 cm in length.

*Stigma shape.*—Round, about 1 mm in diameter.

*Stigma color.*—165B.

*Style color.*—179C and about 1.4 cm in length.

*Ovary color.*—12C and about 2 mm in diameter.

Fruit:

*Type/appearance.*—Six-valved, dehiscent, broad ellipsoidal capsule.

*Length.*—About 8 mm.

*Diameter.*—About 7 mm.

*Immature color.*—144A.

*Mature color.*—200C. Each capsule contains many seeds that are about 5 mm long, 3 mm wide, and 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'Coral Magic', as illustrated and described herein.

* * * * *